US012616645B2

(12) United States Patent
Shamp

(10) Patent No.: US 12,616,645 B2
(45) Date of Patent: May 5, 2026

(54) WATER SOLUBLE SHAMPOO CONTAINER

(71) Applicant: Furlosophy Petcare LLC, Atlanta, GA (US)

(72) Inventor: Gaylin Shamp, Atlanta, GA (US)

(73) Assignee: Furlosophy Petcare LLC, Atlanta, GA (US)

( * ) Notice: Subject to any disclaimer, the term of this patent is extended or adjusted under 35 U.S.C. 154(b) by 391 days.

(21) Appl. No.: 18/352,068

(22) Filed: Jul. 13, 2023

(65) Prior Publication Data

US 2024/0016710 A1     Jan. 18, 2024

Related U.S. Application Data

(60) Provisional application No. 63/389,188, filed on Jul. 14, 2022.

(51) Int. Cl.
*C11D 1/00*          (2006.01)
*A61K 8/11*          (2006.01)
(Continued)

(52) U.S. Cl.
CPC ................ *A61K 8/11* (2013.01); *A61K 8/466* (2013.01); *A61K 8/737* (2013.01); *A61Q 5/02* (2013.01); *C11D 1/143* (2013.01); *C11D 3/0031* (2013.01); *C11D 3/222* (2013.01); *C11D 17/044* (2013.01); *C11D 17/046* (2013.01); *A61K 2800/48* (2013.01); *A61K 2800/87* (2013.01); *C11D 2111/12* (2024.01)

(58) Field of Classification Search
CPC .......... A61K 8/11; A61K 8/466; A61K 8/737; A61K 2800/48; A61K 2800/87; A61K 8/73; A61K 2800/31; A61Q 5/02; A61Q 19/10; C11D 1/143; C11D 3/0031; C11D 3/222; C11D 17/044; C11D 17/046; C11D 2111/12
USPC ......................................................... 510/120
See application file for complete search history.

(56) References Cited

U.S. PATENT DOCUMENTS 7,507,699 B2      3/2009  Burt et al.
11,045,397 B2 *   6/2021  Stern ........................ A61K 8/11
(Continued)

FOREIGN PATENT DOCUMENTS

DE      202009009335 U1    10/2009
DE      202022103077 U1    7/2022
(Continued)

OTHER PUBLICATIONS

"DisSolves is Changing the Way the World Uses Drink Mixes", DisSolves, The Food Pod, Retrieved: Feb. 24, 2023, 2 pgs.
(Continued)

*Primary Examiner* — Eisa B Elhilo
(74) *Attorney, Agent, or Firm* — BEKIARES ELIEZER LLP

(57)          ABSTRACT

The present disclosure provides a single-use cleanser pod including a cleanser that is substantially free of water. The cleanser may be made up of a surfactant and a thickening agent. A water-soluble film may surround the cleanser. The film may have an outer surface configured to interact with an external environment, and an inner surface defining a cavity that retains the cleanser. The cleanser may be configured to form a cleaning solution when mixed with a measured amount of water.

20 Claims, 3 Drawing Sheets

(51) Int. Cl.

| | |
|---|---|
| *A61K 8/46* | (2006.01) |
| *A61K 8/73* | (2006.01) |
| *A61Q 5/02* | (2006.01) |
| *C11D 1/14* | (2006.01) |
| *C11D 3/00* | (2006.01) |
| *C11D 3/22* | (2006.01) |
| *C11D 17/04* | (2006.01) |

(56) References Cited

U.S. PATENT DOCUMENTS

| | | | |
|---|---|---|---|
| 2014/0037703 A1* | 2/2014 | Dihora | D06M 23/12 |
| | | | 510/438 |
| 2015/0136637 A1 | 5/2015 | Meier et al. | |
| 2016/0298061 A1 | 10/2016 | Reichert et al. | |
| 2016/0317397 A1 | 11/2016 | Wenz et al. | |
| 2017/0369824 A1 | 12/2017 | Sunder et al. | |

| | | | |
|---|---|---|---|
| 2019/0216699 A1* | 7/2019 | Stern | A61Q 19/10 |
| 2021/0128415 A1* | 5/2021 | Stern | A61K 8/42 |
| 2021/0388295 A1 | 12/2021 | Mowbray | |
| 2023/0047064 A1 | 2/2023 | Ahn et al. | |

FOREIGN PATENT DOCUMENTS

| | | |
|---|---|---|
| EP | 0194813 A2 | 9/1986 |
| FR | 266348 A1 | 3/1992 |

OTHER PUBLICATIONS

"Water-Soluable Film for Packaging of Detergent, Fertilizers, and Pesticide", Copyright © Guangdong Proudly New Material Technology Corp., Retrieved: Feb. 24, 2023, 2 pgs.

"Customized PVA Water Soluble film, Solid Powder Disposable Water Soluble Pouches", Retrieved: Feb. 24, 2023, 2 pgs.

* cited by examiner

WATER SOLUBLE SHAMPOO CONTAINER

RELATED APPLICATION

Under provisions of 35 U.S.C. § 119(g), the Applicant claims the benefit of U.S. Provisional Application No. 63/389,188 filed on Jul. 14, 2022, which is incorporated herein by reference.

It is intended that each of the referenced applications may be applicable to the concepts and embodiments disclosed herein, even if such concepts and embodiments are disclosed in the referenced applications with different limitations and configurations and described using different examples and terminology.

FIELD OF DISCLOSURE

The present disclosure generally relates to cleanser containers, and more specifically to water-soluble single-use containers for a cleanser.

BACKGROUND

Cleansers, such as shampoos for animals (e.g., pets), humans, upholstery, and/or other items are typically sold in liquid/gel or powder formats. In some situations, the cleanser may be packaged for single use. Such single use packages can render the cleanser relatively bulky and difficult to store. Moreover, the single use packages create excessive plastic waste. Non-refillable bulk packaging can also be larger than needed and difficult to store.

Still further, traditional shampoos contain a relatively high percentage of water, increasing both weight and volume for storage. The increased weight and volume are not typical issues for most household storage, but may be undesirable in some situations, such as when camping or backpacking.

Moreover many cleansers contain myriad harsh chemicals, which can cause allergic reaction upon exposure to a user's skin, or can cause discomfort, illness, or death upon ingestions.

When using cleansers, rinse time can be a factor for ease of use. In particular, for pets, a bath can be stress-inducing, as it is unfamiliar and constraining. Moreover, for some users (e.g., professional groomers), rinse time can affect a number of groomings possible in a single day, both in terms of the length of time a single grooming takes, and the amount of water required to rinse the cleanser from the animal.

Thus, there is a need for a bulk-free single-use packaging for a simple, safe cleanser that does not create excess plastic waste, and for a cleanser that rinses away quickly and efficiently.

BRIEF OVERVIEW

This brief overview is provided to introduce a selection of concepts in a simplified form that are further described below in the Detailed Description. This brief overview is not intended to identify key features or essential features of the claimed subject matter. Nor is this brief overview intended to be used to limit the claimed subject matter's scope.

In an aspect, the present disclosure provides a single-use cleanser pod including a cleanser that is substantially free of water. The cleanser may be made up of a surfactant and a thickening agent. A water-soluble film may surround the cleanser. The film may have an outer surface configured to interact with an external environment, and an inner surface defining a cavity that retains the cleanser. The cleanser may be configured to form a cleaning solution when mixed with a measured amount of water.

In another aspect, the disclosure relates to a method comprising providing a single-use cleanser pod. The single use cleanser pod may include a cleanser that is substantially free of water, the cleanser being formed from a surfactant and a thickening agent. The pod may further include a water-soluble film surrounding the cleanser, the film comprising an outer surface configured to interact with an external environment, and an inner surface defining a cavity that retains the cleanser. The method further includes introducing the cleanser pod to a measured amount of water, such that the water-soluble film dissolves, and agitating the cleanser and the water to form a cleaning solution.

Both the foregoing brief overview and the following detailed description provide examples and are explanatory only. Accordingly, the foregoing brief overview and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicant. In addition, the drawings may contain other marks owned by third parties and are being used for illustrative purposes only. All rights to various trademarks and copyrights represented herein, except those belonging to their respective owners, are vested in and the property of the Applicant. The Applicant retains and reserves all rights in its trademarks and copyrights included herein, and grants permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure. In the drawings.

DETAILED DESCRIPTION

Figure 1:
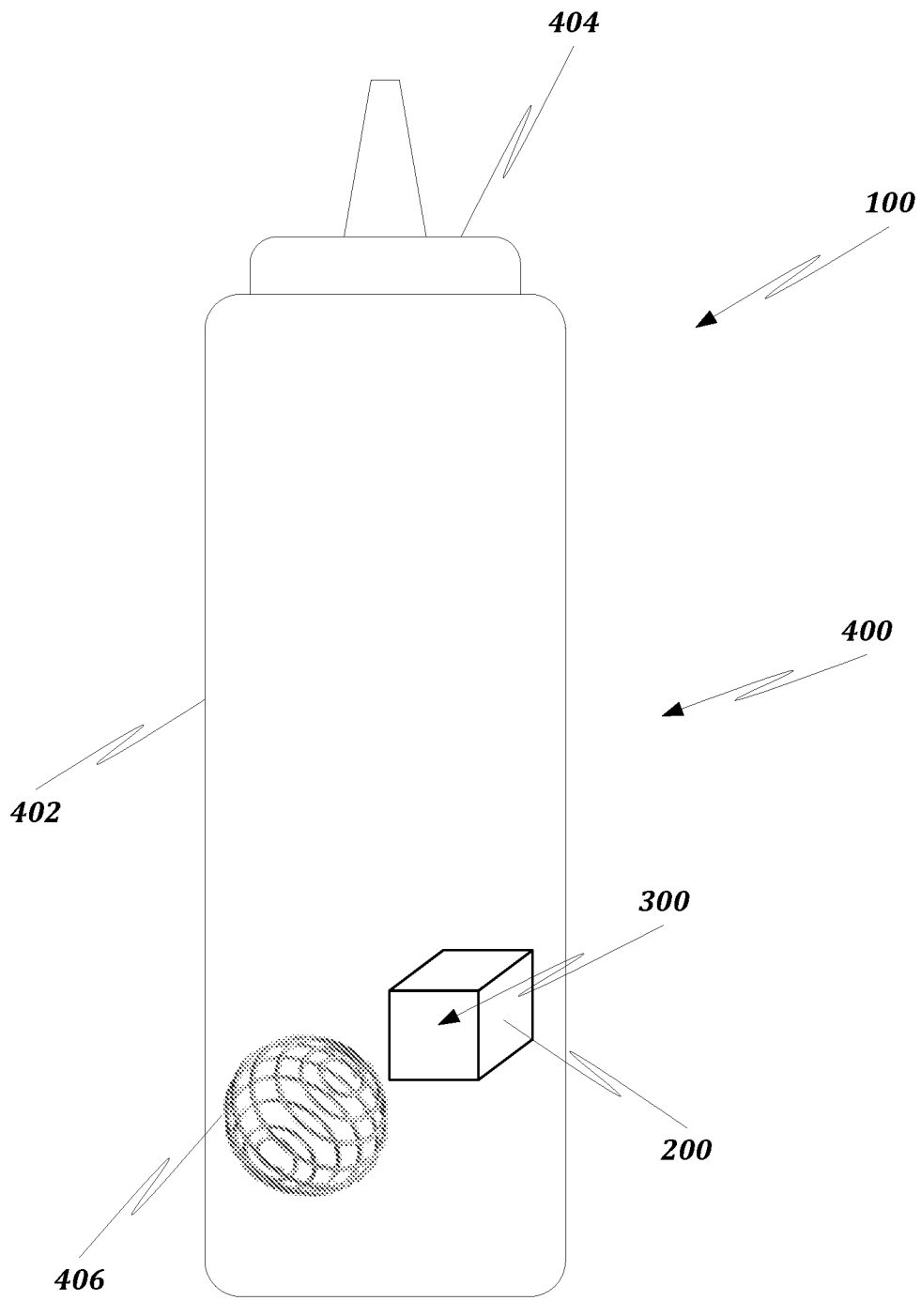
FIG. 1 illustrates a single use cleansing pod system including a single-use cleanser pod and a reusable mixing device.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Regarding applicability of 35 U.S.C. § 112, 16, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

The present disclosure includes many aspects and features. Moreover, while many aspects and features relate to, and are described in, the context of a water-soluble cleanser container, embodiments of the present disclosure are not limited to use only in this context.

I. Apparatus Overview

This overview is provided to introduce a selection of concepts in a simplified form that are further described below. This overview is not intended to identify key features or essential features of the claimed subject matter. Nor is this overview intended to be used to limit the claimed subject matter's scope.

Disclosed herein is a cleanser in a water-soluble container. The cleanser may be used for cleaning an animal, such as a pet (e.g., a dog, a cat, etc.). Additionally or alternatively, the cleanser may be adapted to clean human skin, human hair, clothes, fabric, and/or upholstery. In some embodiments, the container may comprise a pod. The pod may be formed from a film that dissolves when in contact with water. As a particular example, the film may be a GA Grade dissolvable film. The pod may be formed as a container having one of various shapes, such as a sphere, a cube, a rectangular prism, a cylinder, or any other shape that is suitable for containing the cleanser. The pod may have an outer surface, an inner surface, and an interior cavity surrounded by the inner surface.

A cleanser may be enclosed within the interior cavity of the pod. In some embodiments, the cleanser may be formed as a powder that contains no water. Alternatively, the cleanser may be formed as a gel or other liquid that contains no water. The cleanser may be formed in any way that allows for a water-free cleanser to be encased by the pod. Preferably, the weight of the powdered cleanser in the pod is approximately five (5) grams, though the weight may vary depending on the exact makeup of the cleanser. In embodiments, the cleanser may comprise one or more mild surfactants and one or more thickening agents.

Embodiments of the present disclosure may comprise methods, systems, and components comprising, but not limited to, at least one of the following:

A. A Pod; and

B. A Cleanser;

In some embodiments, the present disclosure may provide an additional set of components for further facilitating the system. The additional set of components may comprise, but not be limited to:

C. A Mixing Device.

Details with regards to each component is provided below. Although components are disclosed with specific functionality, it should be understood that functionality may be shared between components, with some functions split between components, while other functions duplicated by the components. Furthermore, the name of the component should not be construed as limiting upon the functionality of the component. Moreover, each stage disclosed within each component can be considered independently without the context of the other stages within the same component or different components. Each stage may contain language defined in other portions of this specifications. Each stage disclosed for one component may be mixed with the operational stages of another component. In the present disclosure, each stage can be claimed on its own and/or interchangeably with other stages of other components.

The following depicts an example of a method of a plurality of methods that may be performed using at least one of the aforementioned components. Furthermore, although the stages of the following example method are disclosed in a particular order, it should be understood that the order is disclosed for illustrative purposes only. Stages may be combined, separated, reordered, and various intermediary stages may exist. Accordingly, it should be understood that the various stages, in various embodiments, may be performed in arrangements that differ from the ones claimed below. Moreover, various stages may be added or removed without altering or deterring from the fundamental scope of the depicted methods and systems disclosed herein.

Consistent with embodiments of the present disclosure, a method may be performed by at least one of the aforementioned components. The method may be embodied as, for example, but not limited to, computer instructions, which when executed, perform the method. The method may comprise the following stages:

Filling a mixing device with a measured amount of water;

Placing a pod comprising a film surrounding a cleanser in the mixing device;

Agitating the pod and the water in the mixing device to dissolve the film and create a measured amount of cleaning fluid;

Dispensing the cleaning fluid from the mixing device to clean an object; and

Rinsing the cleaning fluid from the object.

Both the foregoing overview and the following detailed description provide examples and are explanatory only. Accordingly, the foregoing overview and the following detailed description should not be considered to be restrictive. Further, features or variations may be provided in addition to those set forth herein. For example, embodiments may be directed to various feature combinations and subcombinations described in the detailed description.

II. System Configuration

In some embodiments, a single use cleansing pod system 100 may include a cleanser 300 contained in a single use or pod 200, and a container 400. The cleanser 300 and container 200 may be mixed with water using a mixing device 400 to form a cleaning fluid. The device 100 may comprise a distributed set of components, including, but not limited to:

A. A Pod

Figure 2:
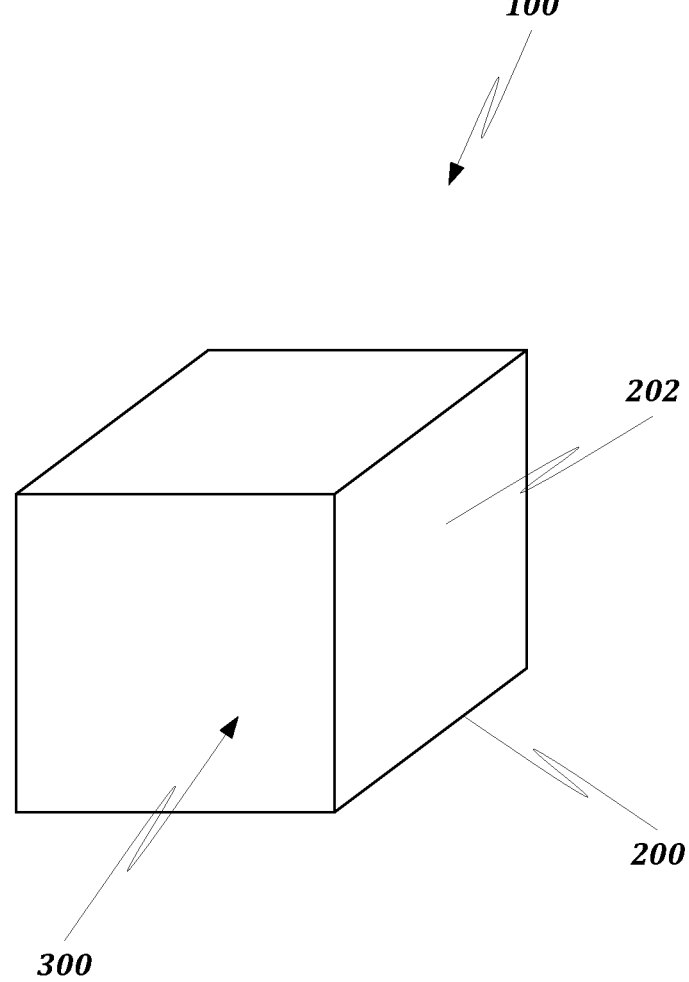
FIG. 2 is a perspective view of the single-use cleanser pod.
Figure 3:
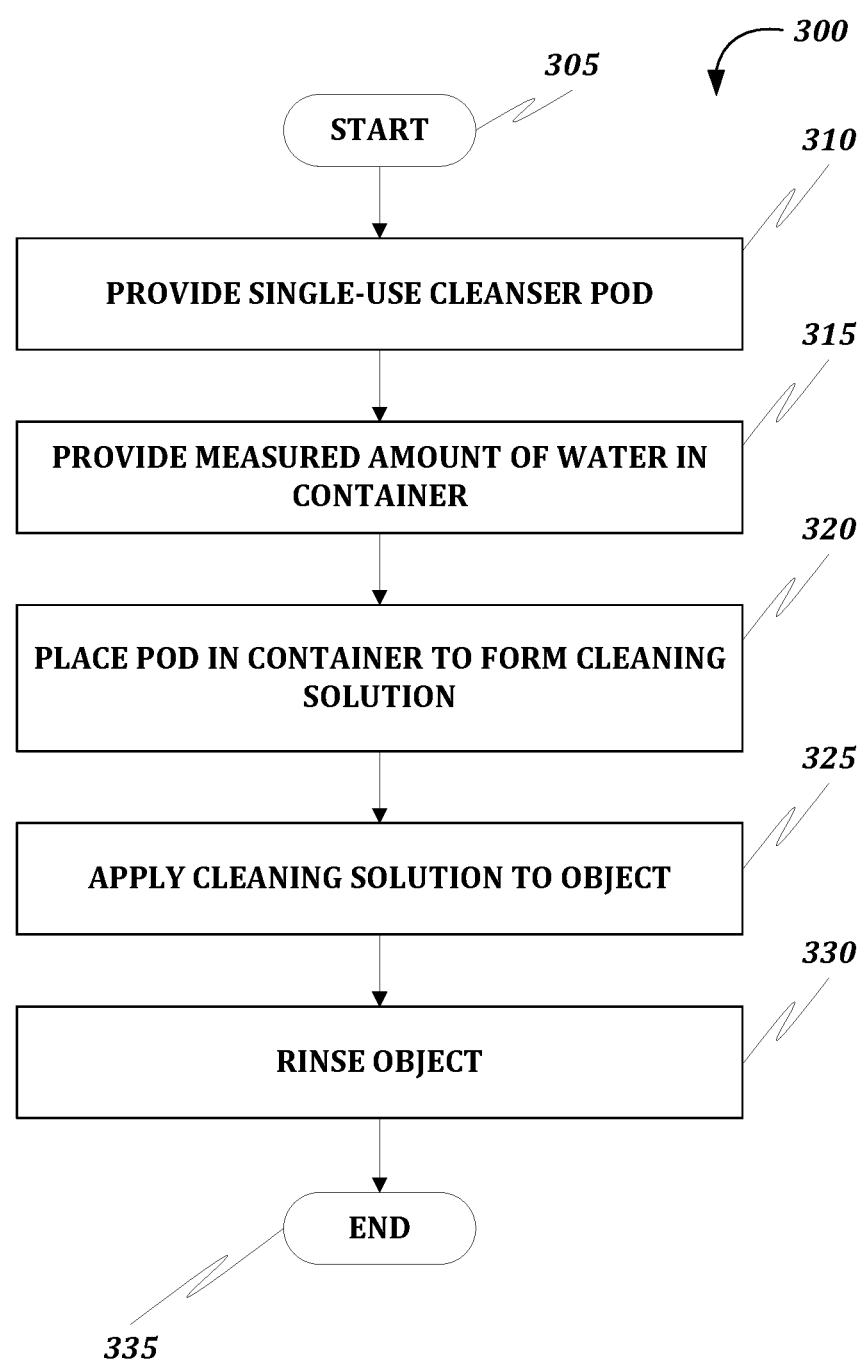
FIG. 3 is a flowchart illustrating a method of use thereof.

As shown in FIGS. 1-2, the device 100 may include a pod 200. The pod 200 may be formed from a film 202. In embodiments, the film 202 may be formed from a water-soluble material, such that the film dissolves when in contact with water.

In some embodiments, the water-soluble film 202 may be formed from a polyvinyl resin. The film 202 may be a transparent, odorless film. The film 202 may be thick enough and flexible enough to resist punctures, rips, and tears while dry, but may have properties that allow the film to dissolve quickly when in contact with water. For example, the film 202 may dissolve in 30 seconds when exposed to (e.g., immersed in) water. In some embodiments, the film may be dissolvable in warm and/or cold water, such as water below 100 degrees Fahrenheit, water below 90 degrees Fahrenheit, and/or water below 80 degrees Fahrenheit. In some embodiments, the dissolution time may be reduced by mechanical agitation of the water and the pod 200. The film may have a thickness in the range of 30-70 microns. As one non-limiting example, the film 202 may be a 50 micron copolymer cold water-soluble film, such as those produced by Aicello or Solublon Corporations.

The film 202 may be formed into a three-dimensional shape to define a shape of the pod 200. For example, the pod 200 may be shaped as a sphere, a cylinder, a cube, or any other shape sufficient to retain a cleanser. In embodiments the pod 200 may have an inner surface that defines a cavity or void to be filled with the cleanser and prevents the cleanser from escaping the pod. The pod 200 may have an outer surface that prevents contamination of the cleanser from material outside the pod.

In some embodiments, the pod 200 may be formed from a single piece of the film 202. Alternatively, the pod 200 may be formed from multiple pieces of the film 202. The multiple pieces of the film 202 may be joined by, for example, chemical adhesives, heat welds, and/or any other known technique to attach the film to itself.

B. A Cleanser

As shown in FIG. 2, a single use cleansing pod system 100 may include a cleanser 300. The cleanser 300 may be formed as any cleanser without water. For example, the cleanser 300 may be formed as a powder that contains no water, a gel or fluid that contains no water, and/or any other formulation that avoids use of water. In embodiments, the cleanser 300 may be a low-lather cleanser that produces a relatively small amount of foam when mixed with water and agitated.

The cleanser 300 may include one or more surfactants, and one or more thickeners or thickening agents. In some embodiments, the cleanser 300 may optionally include additional ingredients to enhance the experience of using the cleanser.

The surfactant may be selected from a group of natural and/or synthetic surfactants, including (but not limited to) sodium cocoyl Isethionate, cocamidopropyl betaine, decyl glucoside, lauryl glucoside, sodium lauroyl sarcosinate, cetrimonium chloride, sodium dodecyl sulfate, cocamide monoethanolamine, ammonium lauryl sulfate, other alkyl sulfates, one or more other anionic surfactants, one or more other nonionic surfactants, one or more other amphoteric surfactants, and/or any other surfactant that is safe for use on humans and other animals may be included in the one or more surfactants that make up the cleanser. In some embodiments the one or more surfactant may make up approximately 60-90 percent by weight of the cleanser. As examples, the one or more surfactants may make up 60-90 wt %, 65-90 wt %, 70-90 wt %, 75-90 wt %, 75-85 wt %, 80 wt %, and/or any percentage sufficient to provide cleansing to an object. The surfactant should include no water, and is preferably a powder or gel.

The one or more thickeners or thickening agents may be selected from a group of natural and/or synthetic thickeners including (but not limited to) guar hydroxypropyltrimonium CL, guar gum, cellulose derivatives such as hydroxyethyl cellulose (HEC) and/or hydroxypropyl methylcellulose (HPMC), xanthan gum (e.g., Xanthan Gum 80 USP/NF FCC K), carbomers, acrylates copolymer, cetearyl alcohol, polyethylene glycol (PEG)-150 distrearate, hydroxypropyl methylcellulose, PEG-120 methyl glucose dioleate, POE (2) Oleyl Amine, and/or any other thickener or thickening agent that is safe for use on humans and other animals. In embodiments, guar hydroxypropyltrimonium CL or another cationic thickener may be particularly beneficial because it neutralizes negative charges on hair strands, helping to reduce static charge forces between hair strands. In some embodiments the one or more thickeners or thickening agents may make up approximately 10-40 percent by weight of the cleanser. For example, the one or more thickeners may make up 10-40 wt %, 15-35 wt %, 15-30 wt %, 15-25 wt %, 20-25 wt %, and/or any percentage to produce a suitable cleansing liquid when mixed with a measured amount of water. In some embodiments, the one or more thickening agents may include multiple thickening agents. For example, the cleanser 300 may include two thickening agents. As a particular example, the cleanser 300 may include guar hydroxypropyltrimonium CL and xanthan gum. As a particular non-limiting example, guar hydroxypropyltrimonium CL may form 4-15% by weight (e.g., 7 wt %) of the cleanser 300, and xanthan gum may form 5-25% by weight (e.g., 13 wt %) of the cleanser. The one or more thickeners or thickening agents should include no water, and is preferably a powder or gel. In embodiments, the one or more thickeners may be selected to form a relatively thin cleaning solution when mixed with water, such that the mixed cleaning solution rinses away relatively quickly and with a reduced amount of water, when compared to conventional cleaning solutions.

In some embodiments, the cleanser 300 may optionally include one or more additional ingredients to enhance the experience of using the cleanser. For example, the cleanser may include one or more conditioning agents, one or more moisturizers, one or more chelating agents, one or more pH adjusters or buffers, and/or any other additives to improve the appearance, smell, stability, or shelf life of the cleanser 300.

The cleanser 300 may optionally include one or more conditioning agents (e.g., dimathicone, PEG-7 glyceryl cocoate, polyquaternium-7, polyquaternium-10, etc.). A conditioning agent may be an additive used to enhance the feel, appearance, fullness, lubricity, reflectance, and general manageability of hair and skin after using the cleanser. The conditioning agent may be a cationic surfactant or a polymer that clings to the hair or adsorbs onto the skin, leaving a pleasant silky feel.

The cleanser 300 may optionally include one or more moisturizers (e.g., glycerin, allantoin, hydroxyethyl urea, trehalose, etc.) used for protecting, moisturizing, and lubricating the skin. The one or more moisturizers may modify the rate of water loss of skin. With different active ingredients, the moisturizers may fall into one or more of two categories: occlusives and humectants.

The cleanser 300 may optionally include one or more chelating agents (e.g., Ethylenediaminetetraacetic Acid Disodium, etc.). Chelating agents bind to iron (e.g., $Fe^{2+}$ and/or $Fe^{3+}$), magnesium (e.g., $Mg^{2+}$), and/or calcium (e.g., $Ca^{2+}$) ions, forming water-soluble complexes in an aqueous solution, thus preventing these metal ions from bonding to the surfactants. In this way, chelating agents contribute to softening the water and maintaining the effectiveness of the surfactants in the formulas.

The cleanser 300 may optionally include one or more buffers or pH adjusters (e.g., sodium hydroxide, citric acid, etc.). The pH adjusters are ingredients to adjust the pH value of a formula to achieve and maintain the desired efficacy. In detergent, personal care, and cosmetic formulas, pH adjusting is commonly done either by increasing the alkalinity (with sodium hydroxide) or increasing the acidity (with citric acid). In some cases, citric acid may be added into the formula not only to achieve a desired pH range of the formula itself, but also to play a role as a buffering agent for the aqueous solution to maintain a stable pH range when the final product is used.

The cleanser 300 may optionally include one or more additives, such as perfumes or dyes to adjust an odor and/or a color of the cleanser and/or one or more preservatives to extend a shelf life of the cleanser. The additives may improve appearance, smell, and/or stability of a cleanser, and may extend a shelf life of the cleanser.

C. A Mixing Device

As shown in FIG. 1, the system 100 may include a reusable mixing device 400 to mix the cleanser 300 (and the dissolvable pod or container 200) with a measured amount of water. The mixing device 400 may include at least a container 402 for receiving and retaining the measured amount of water. In embodiments, the container 402 may include one or more lines or other indicia to indicate liquid measurements corresponding to one or more levels to which water may be added to the container to form a cleaning solution. The pod 200 containing the cleanser 300 may be added to the container 402 to allow the film 202 to contact the water and begin the dissolving process. As the film 202 dissolves, the cleanser 300 may contact the water, and may mix with the water to form a cleaning solution.

In some embodiments, a mechanical agitation may be used to facilitate dissolution of the film 202 and/or mixing of the cleanser 300 with the water. As one example, the contents of the container 402 (e.g., the pod 200 containing the cleanser 300 and the water may be mixed using an implement such as a stirrer, a spoon, a paddle, etc. In some embodiments, a motorized or mechanized stirring mechanism such as a blender or automatic stirrer may be used).

As another example, the mixing device 400 may include a lid 404 designed to form a relatively water-tight seal with the container 402. For example, the lid 404 may be a removable lid that may attach to the container 402 using a snap fit, a friction fit, a threaded engagement, or the like. With the lid 404 attached to the container 402, a user may mechanically agitate the mixing device 400 (and the contents thereof) by shaking.

In some embodiments, the mixing device 400 may optionally include a wire whisk 406. The wire whisk 406 may comprise an approximately spherical wire that is inserted into the container 402 prior to attachment of the lid 404. The wire whisk 406 may help facilitate mechanical agitation of the contents, thereby helping to more quickly form the cleaning solution.

III. Apparatus/System Use

The following depicts an example of a method of a plurality of methods that may be performed by at least one of the aforementioned components. Various hardware components may be used at the various stages of operations disclosed with reference to each component.

Furthermore, although the stages of the following example method are disclosed in a particular order, it should be understood that the order is disclosed for illustrative purposes only. Stages may be combined, separated, reordered, and various intermediary stages may exist. Accordingly, it should be understood that the various stages, in various embodiments, may be performed in arrangements that differ from the ones claimed below. Moreover, various stages may be added or removed from the without altering or deterring from the fundamental scope of the depicted methods and systems disclosed herein.

Consistent with embodiments of the present disclosure, a method 300 may be performed by at least one of the aforementioned components.

The method 300 may begin at stage 305, and may proceed to stage 310, where a pod is provided. The pod may include a cleanser that contains no water surrounded by a film to form a pod. The pod may be formed in various shapes, including (but not limited to) approximately spheric, approximately cubic, approximately cylindric, or any other shape that contains the cleanser. The cleanser may be formed as a powder, gel, or other fluid that contains no water. In some embodiments, the pod may be provided in a wrapping to prevent exposure to air, as the humidity within the air may cause the film to decay. In other embodiments, the film may be sufficiently durable to withstand the humidity of the air.

After stage 310, a measured amount of water may be provided in a container in stage 315. The measured amount of water may be, for example, between 12 fluid ounces and 24 fluid ounces. In some embodiments, the measured amount of water may be 20 fluid ounces. The container may be a special purpose container for mixing the water with the pod. Alternatively, the container may be any container sized sufficiently to retain the water and the pod.

In stage 320, a user may place the pod in the container such that the pod contacts the water to dissolve. In embodiments, the user may agitate the solution of the water and the pod to facilitate dissolution of the film and mixing of the cleanser with the water to form a cleaning solution. The agitation may comprise any mechanical agitation, such as mixing, stirring, shaking, etc. The agitation may be performed manually, or may be performed with mechanical assistance, e.g., using a mixer, blender, automated stirrer, or the like. In embodiments, the cleanser, when mixed with water, preferably forms a low-foam cleaning solution.

In stage 325, the user may apply the mixed cleaning solution to an object, such as (but not limited to) the user themself, another human, an animal (e.g., a pet, such as a dog, a cat, a rabbit, a ferret, and/or the like), an article of clothing, upholstery fabric, or any other object in need of cleaning.

In stage 330, the user may rinse the cleaning solution from the object using fresh water. The rinsing process may be reduced when compared to conventional shampoos or cleansers due to the relatively thin cleaning solution and relatively mild thickening agents. In this way, the rinsing process may be completed faster than with conventional cleaning solutions, and using less water. After rinsing, the process 300 may end at stage 335.

IV. CLAIMS

While the specification includes examples, the disclosure's scope is indicated by the following claims. Furthermore, while the specification has been described in language specific to structural features and/or methodological acts, the claims are not limited to the features or acts described above. Rather, the specific features and acts described above are disclosed as examples for embodiments of the disclosure. Insofar as the description above and the accompanying drawing disclose any additional subject matter that is not within the scope of the claims below, the disclosures are not dedicated to the public and the right to file one or more applications to claims such additional disclosures is reserved.

The following is claimed:

1. A cleanser pod comprising:
a cleanser that is free of water in powder form, the cleanser including:
   a surfactant, and
   a thickening agent; and a water-soluble film surrounding the cleanser, the film comprising an outer surface configured to interact with an external environment, and an inner surface defining a cavity that retains the cleanser;
wherein the cavity is sized to retain approximately five grams of the cleanser; and
wherein the cleanser is configured to form a cleaning solution when mixed with a measured amount of water.

2. The cleanser pod of claim 1, wherein the film comprises a cold-water soluble film.

3. The cleanser pod of claim 2, wherein the film has a thickness of approximately 50 microns.

4. The cleanser pod of claim 1, wherein the surfactant comprises sodium cocoyl isethionate.

5. The cleanser pod of claim 4, wherein the cleanser comprises sodium cocoyl isethionate in a range of 55 wt %-90 wt %.

6. The cleanser pod of claim 4, wherein the thickening agent comprises one or more of Guar Hydroxypropyltrimonium CL and xanthan gum.

7. The cleanser pod of claim 6, wherein the cleanser comprises Guar Hydroxypropyltrimonium CL in a range of 4 wt %-15 wt % and xanthan gum in a range of 5 wt %-25 wt %.

8. A cleanser pod system comprising:
the cleanser pod of claim 1; and
a mixing device comprising:
   a container configured to receive and retain a measured amount of water, and
   a mechanical agitator that facilitates mixing of the cleanser with water in the container.

9. The cleanser pod system of claim 8, further comprising a lid configured to seal the container.

10. The cleanser pod system of claim 9, wherein the mechanical agitator comprises a wire whisk.

11. The cleanser pod system of claim 8, wherein the mechanical agitator comprises a stirrer.

12. The cleanser pod system of claim 8, wherein the mechanical agitator comprises a blender.

13. A method comprising:
providing a single-use cleanser pod, the single use cleanser pod including:
a cleanser that is free of water in powder form, the cleanser including:
a surfactant, and
a thickening agent; and
a water-soluble film surrounding the cleanser, the film comprising an outer surface configured to interact with an external environment, and an inner surface defining a cavity that retains the cleanser;
wherein the cavity is sized to retain approximately five grams of the cleanser;
introducing the cleanser pod to a measured amount of water, such that the water-soluble film dissolves; and
agitating the cleanser and the water to form a cleaning solution.

14. The method of claim 13, further comprising:
applying the cleaning solution to an object to be cleaned; and
rinsing the solution from the object to be cleaned.

15. The method of claim 14, wherein the object to be cleaned comprises one of:
a human,
an animal,
an article of clothing, or
an upholstery fabric.

16. A cleanser mixing system comprising:

a container configured to hold a measured amount of water;

a mechanical agitator positioned within the container, the mechanical agitator selected from the group consisting of a whisk, a stirrer, and a blender; and a cleanser pod configured to be introduced into the container, the cleanser pod comprising:

a cleanser that is free of water in powder form, the cleanser including a surfactant and a thickening agent; and a water-soluble film surrounding the cleanser, the film comprising an outer surface configured to interact with the water as an external environment, and an inner surface defining a cavity that retains the cleanser;

wherein the cavity is sized to retain approximately five grams of the cleanser; and wherein the mechanical agitator is configured to agitate the cleanser and the water to form a cleaning solution after the water-soluble film dissolves.

17. The cleanser pod of claim 1, wherein the surfactant comprises sodium cocoyl isethionate and the thickening agent comprises Guar Hydroxypropyltrimonium CL.

18. The cleanser pod of claim 1, wherein the cleanser further comprises a fragrance agent.

19. The cleanser pod of claim 1, wherein the water-soluble film comprises polyvinyl alcohol.

20. The method of claim 13, wherein the measured amount of water is between 100 mL and 500 mL.

* * * * *